United States Patent [19]

Johnson, Jr.

[11] Patent Number: 4,872,448

[45] Date of Patent: Oct. 10, 1989

[54] KNEE BRACE HAVING ADJUSTABLE INFLATABLE U-SHAPED AIR CELL

[76] Inventor: Glenn W. Johnson, Jr., 10 Friar Tuck Cir., Summit, N.J. 07901

[21] Appl. No.: 51,360

[22] Filed: May 19, 1987

Related U.S. Application Data

[63] Continuation-in-part of Ser. No. 921,858, Oct. 22, 1986, abandoned, which is a continuation of Ser. No. 483,448, Apr. 11, 1983, abandoned.

[51] Int. Cl.⁴ ............................................... A61F 5/04
[52] U.S. Cl. .......................... 128/80 C; 128/DIG. 20
[58] Field of Search .......... 128/80 C, 118.1, DIG. 20, 128/80 R, 80 F, 80 H

[56] References Cited

U.S. PATENT DOCUMENTS

| | | | |
|---|---|---|---|
| 891,533 | 6/1908 | Gibbs | 128/DIG. 20 |
| 2,694,395 | 11/1954 | Brown | 128/118 |
| 3,853,123 | 12/1974 | Moore | 128/80 C |
| 4,013,070 | 3/1977 | Harroff | 128/80 C |
| 4,041,940 | 8/1977 | Frankel et al. | 128/80 C |
| 4,090,508 | 5/1978 | Gaylord, Jr. | 128/80 C |
| 4,116,236 | 9/1978 | Albert | 128/80 C |
| 4,186,738 | 2/1980 | Schleicher et al. | 128/80 R |
| 4,201,203 | 5/1980 | Applegate | 128/80 C |
| 4,280,489 | 7/1981 | Johnson, Jr. | 128/80 H |
| 4,287,884 | 9/1981 | Applegate | 128/80 C |
| 4,287,885 | 9/1981 | Applegate | 128/80 C |
| 4,370,978 | 2/1983 | Palumbo | 128/80 C |
| 4,378,009 | 3/1983 | Rowley et al. | 128/DIG. 20 |
| 4,425,912 | 1/1984 | Harper | 128/80 C |
| 4,445,505 | 5/1984 | Labour et al. | 128/80 C |
| 4,628,945 | 12/1986 | Johnson, Jr. | 128/80 H |

Primary Examiner—Edgar S. Burr
Assistant Examiner—Tonya Lamb

[57] ABSTRACT

A knee brace is provided comprising first adjustable means for engaging the knee and providing support to the patella without hindering normal tracking movement thereof, and second adjustable means for fastening said first adjustable means in engagement with the knee. In an alternatively preferred embodiment, at least third adjustable means are provided for engaging the knee and providing enhanced support to the knee joint, namely, in the infra patella region.

18 Claims, 12 Drawing Sheets

KNEE BRACE HAVING ADJUSTABLE INFLATABLE U-SHAPED AIR CELL

RELATED APPLICATIONS

The present application is a continuation-in-part of my prior co-pending application Ser. No. 06/921,858, now abandoned, filed Oct. 22, 1986 which, in turn, is a continuation of my prior application Ser. No. 06/483,448, filed Apr. 11, 1983, now abandoned.

FIELD OF INVENTION

The present invention relates generally to braces, and more specifically to braces adapted to be worn or fitted about the knee in order to stabilize the patella (kneecap).

BACKGROUND ART

Certain abnormalities of the knee including subluxation of the patella, chrondromalacia, patella tendonitis, and Osgood-Schlatter's disease effectively may be treated by use of a knee brace specifically designed to stabilize the knee and promote normal patella tracking. The known devices of this type usually consist of a sleeve fitted about the knee and carrying a pair of live rubber "stays" straddling the patella. The sleeve and stays are maintained in position by a series of circumferentially extending straps held in place by suitable fastening elements, e.g. VELCRO material. These prior art braces, however, are characterized by various disadvantages. They must be firmly engaged about the knee to maintain the rubber stays in their proper supporting relation with the patella and, therefore, are frequently uncomfortable to wear especially when complete functionality of the leg's extensor mechanism is desired. Moreover, these prior devices are difficult to adjust for optimum effect and comfort, and different sizes are necessary to fit different subjects.

DISCLOSURE OF THE INVENTION

Against the foregoing background, it is the primary object of the present invention to provide an improved knee brace which may be used to stabilize the knee and promote normal patella tracking.

It is another important object of the present invention to provide an improved knee brace which may be adjustably secured in a circumferential manner about the knee, and which when so engaged may be separately and independently adjusted to apply stabilizing support to the patella sufficient to maintain normal tracking thereof while optimum comfort and support may be achieved.

Toward the accomplishment of these objectives and advantages, the present invention, briefly summarized, comprises a U-shaped inflatable air cell or bladder adapted to engage the knee, specifically in the regions defined above and along the opposed sides of the patella. The upper and lower portions of the U-shaped air cell have fastened thereto respectively a pair of circumferentially extending flexible straps which may be wrapped around the knee generally above and below the patella to maintain the air cell in its intended engagement. In use, the air cell is placed in position with its upper portion engaging the knee above the patella and its respective arm portions engaging the opposed sides of the patella whereupon the upper and lower circumferential straps are fastened to a comfortable tension. The air cell is then inflated by mouth pressure through a tube and valve until the desired firm supporting pressure against the opposed sides of the patella is achieved. In an alternatively preferred embodiment, a separate inflated air cell is provided in a juxtaposed manner relative to the distal ends of the U-shaped air cell's arm portions to afford supplemental support in the region proximally below the patella, i.e. in the infra patella region.

BRIEF DESCRIPTION OF THE DRAWINGS

The foregoing and still other features and advantages as well as a more complete understanding of the present invention will be made more apparent from a study of the following detailed description of the preferred form of the invention in connection with the accompanying drawings wherein.

BEST MODE OF CARRYING OUT THE INVENTION

Figure 1:
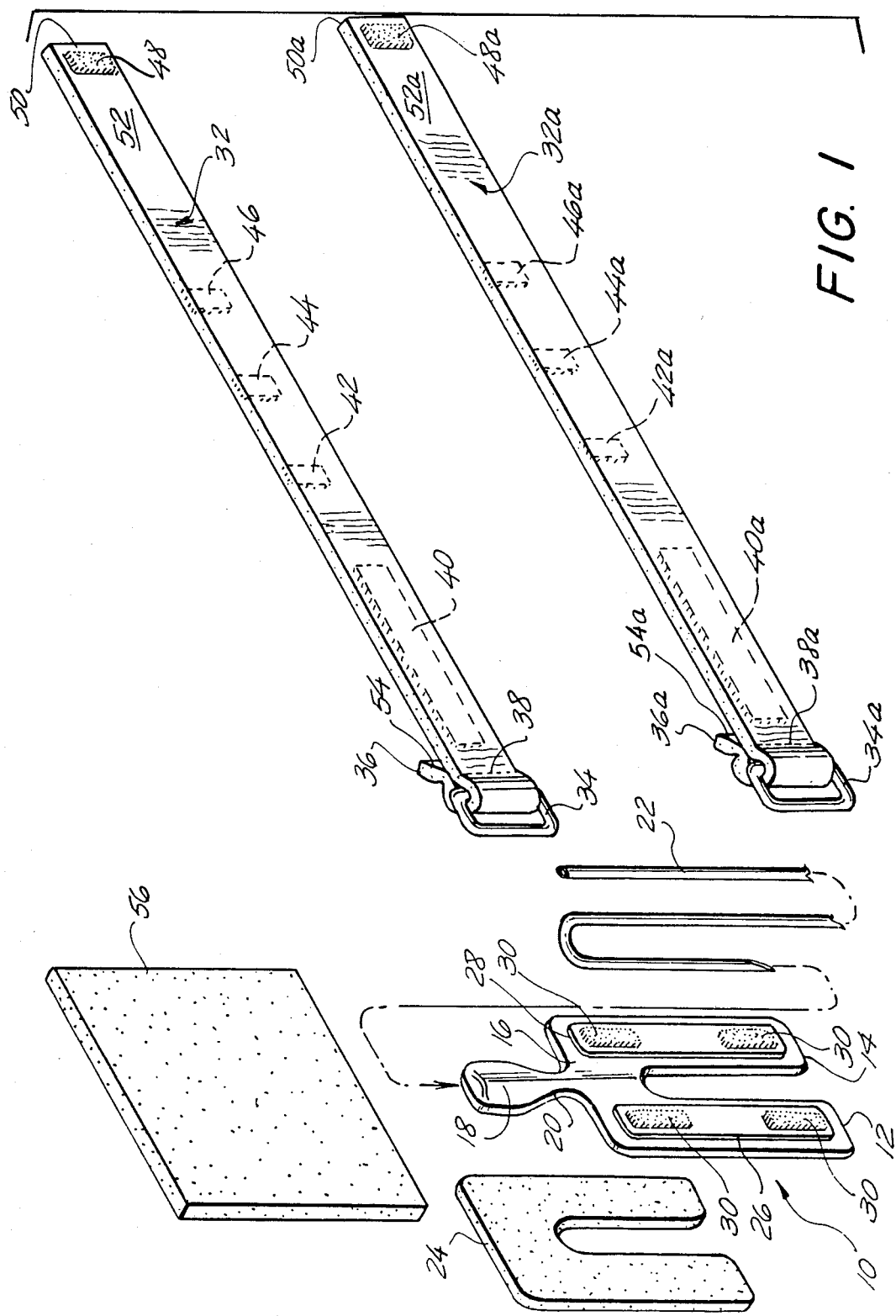
FIG. 1 is a schematic exploded perspective of the constituent parts of the knee brace of the present invention.

Referring initially to FIG. 1 a first preferred embodiment of the invention comprises a flexible, inflatable air cell or bladder generally designated by reference numeral 10 having a pair of opposed, depending arm portions 12, 14 joined by an upper base portion 16 to form generally an upside-down U-shaped configuration, substantially as depicted. A valve member 18 extends upwardly from base portion 16 integrally connected thereto via throat portion 20.

Air cell 10 and its integral valve 18 preferably are fabricated from a pair of co-extensive, opposed flexible plastic sheets (e.g. polyvinyl chloride) each having a thickness in the range of about 10 to 15 mils, and which are bonded together as by heat sealing along their peripheral edges in a known manner. The details of construction of air cell 10 and especially of its integral valve member 18 are fully disclosed in my prior U.S. Pat. No. 4,287,920 granted Sept. 8, 1981, the disclosure of which is hereby incorporated herein by this reference.

Suffice it to say, for purposes of understanding the present invention, air cell 10 may be inflated conveniently by inserting one end of a length of tubing 22 into and through valve 18 and applying mouth pressure to the other end of the tubing. As taught in my prior U.S. Pat. No. 4,287,920, when the tubing is withdrawn from the valve, the latter will automatically self-seal thereby maintaining air cell 10 in its intended inflated condition. The inflated air cell may be said to be semi-compressible because although it will conform to the irregular shape of the knee above and on either side of the patella, the air cell will apply a uniform supporting force or pressure against these regions of the knee as will be made more evident from the ensuing discussion.

In order to provide more comfort to the wearer of the knee brace of the present invention and further, to provide resistance against displacement, a flexible pad 24 of felt or any similar absorbent material, shaped to conform to air cell 10, is affixed to one side of the air cell via a suitable adhesive, for example.

Disposed on the other side of air cell 10, substantially as shown, also via a suitable adhesive, is a pair of stiffeners or stays 26, 28, conforming to arm portions 12, 14, respectively. In turn, each stay 26, 28 has affixed thereto an upper and lower fastening element 30 of VELCRO hook material also substantially as shown.

The purpose of stays 26, 28 is to add further stiffening support to the inflated arm portions 12, 14 of air cell 10. In the preferred embodiment, the stays 26, 28 are fabricated of a molded plastic material (e.g. polyvinyl chloride, or more preferably, Nylon) and each has thickness of 0.093 inches and a width of 0.75 inches. In addition, each stay may be slightly arcuate or curved in in the plane parallel to the air cell to more closely conform to the shape of the patella when air cell 10 is in an inflated condition. In the same preferred embodiment, air cell 10 has a length top-to-bottom of 7 inches, is 4½ inches wide at the base portion 16, and each arm portion has a width of 1.5 inches.

A pair of fastening straps 32, 32a of rectangular elongate shape is provided to adjustably support air cell 10 despite knee size variations. Since the straps 32, 32a are virtually identical, a description of one will apply to both. Upper strap 32 has a fastening ring 34 affixed to one end 36 by forming a loop through the ring substantially as shown and sewing together along seam 38. Affixed to the rear side of upper strap 32, as viewed in FIG. 1, is a first fastening element 40 of conventional matable loop material, and second, third, and fourth fastening elements 42, 44, 46 of conventional matable hook material spaced along the longitudinal extent of the strap substantially as shown. Finally, upper strap 32 includes a fifth fastening element 48 of conventional matable hook material affixed to its front side proximal to distal free end 50. As mentioned, lower strap 32a is virtually identical to upper strap 32 and both straps advantageously may be fabricated from a laminated (double-ply) flexible, but strong material such as that commercially available under the VELCRO trademark. Such material has a front or outer ply 52 of conventional loop matable or fastener material bonded to a rear or inner ply 54 of polyurethane foam. In the preferred embodiment of the present invention, fastening straps 32, 32a are 20 inches in 25 length and 2 inches wide.

Figure 2:
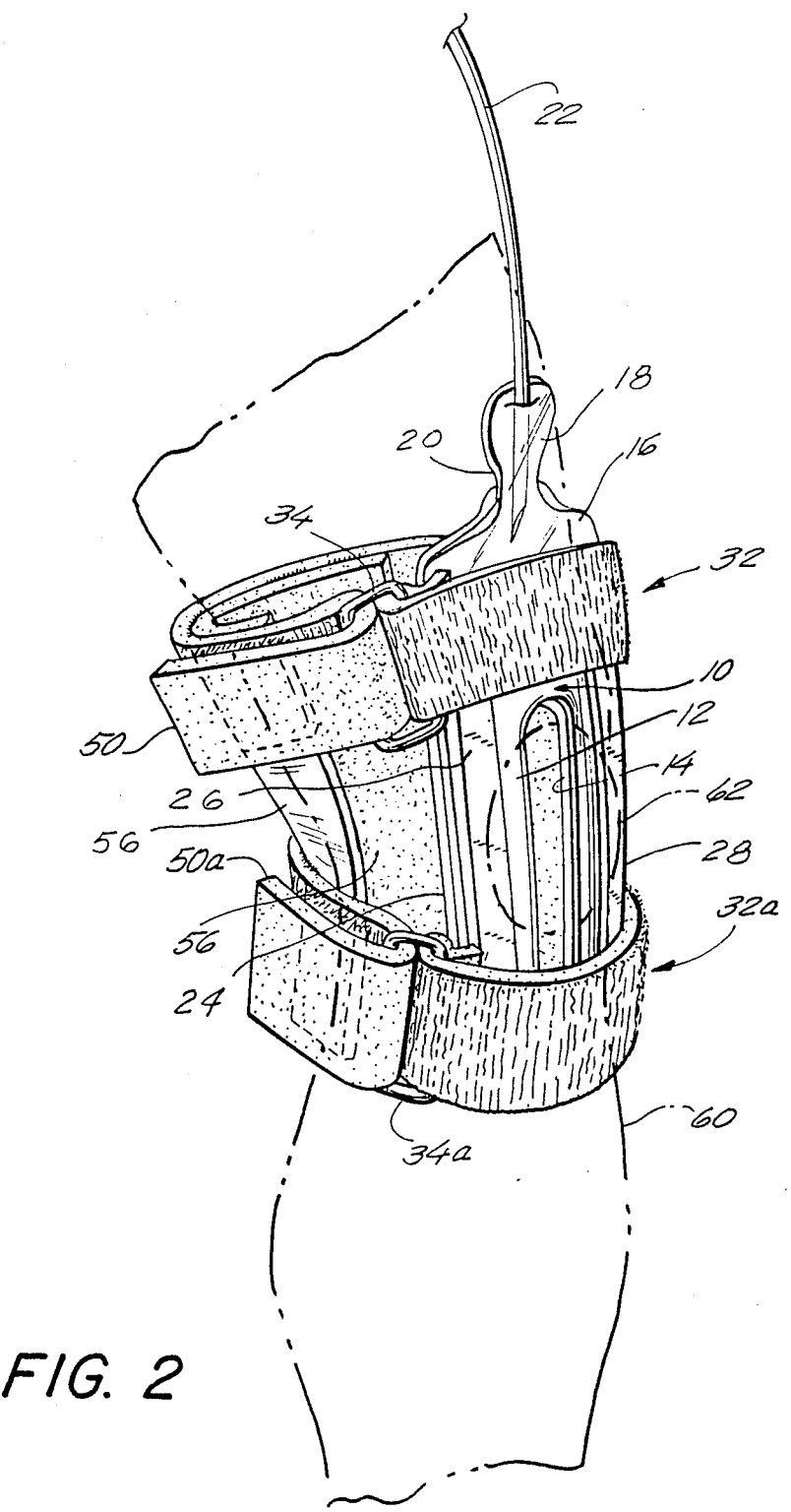
FIG. 2 is a perspective illustration of the knee brace of the present invention fastened in place about an imaginary knee.
Figure 3:
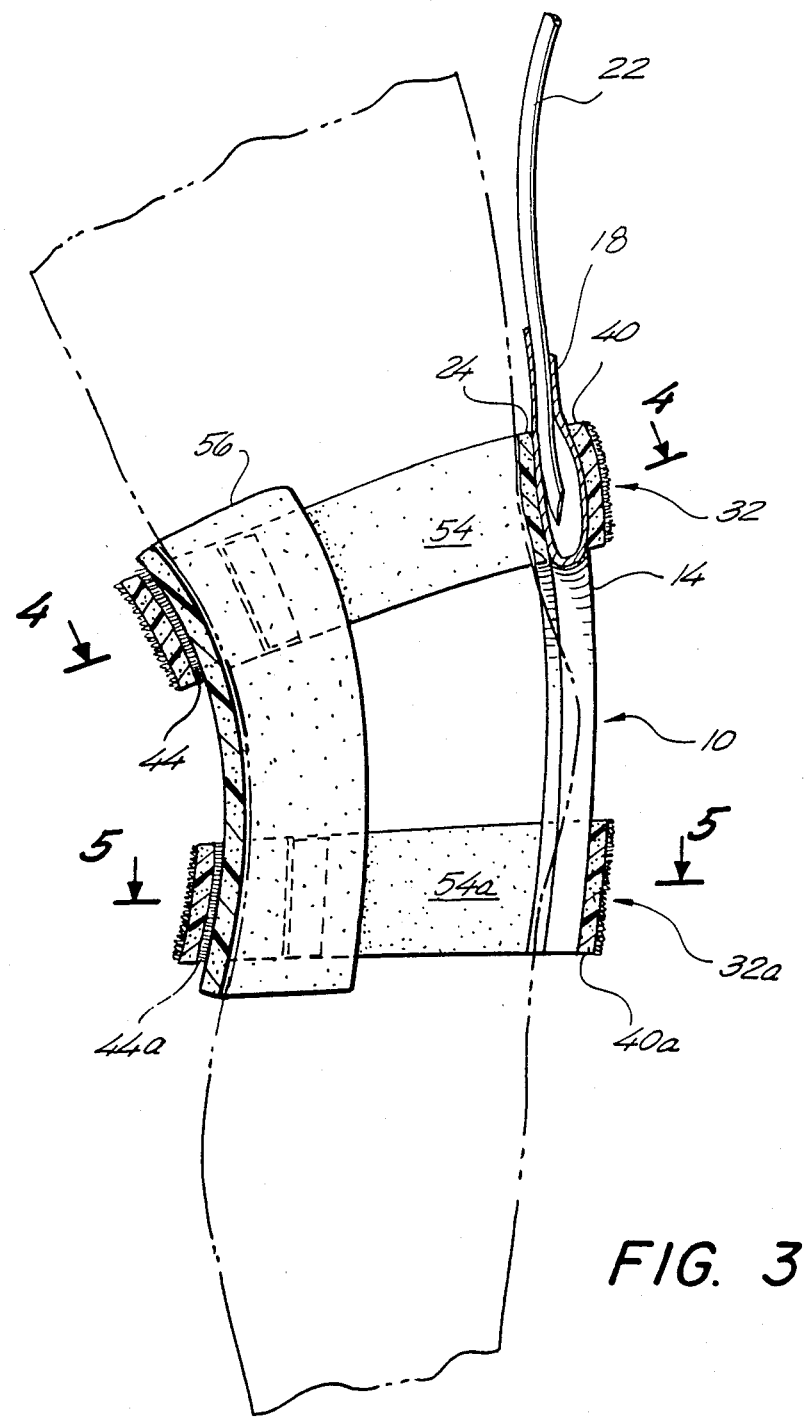
FIG. 3 is a view in elevation of a section defined by a vertical plane passing through the knee brace and imaginary knee of FIG. 2.
Figure 4:
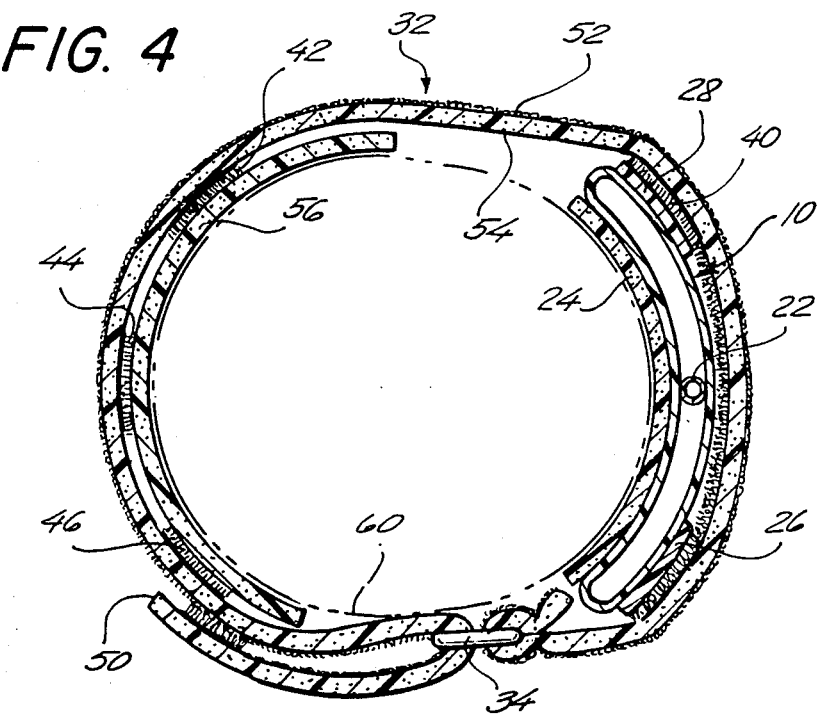
FIG. 4 is a sectional plan view taken along line 4—4 of FIG. 3.
Figure 5:
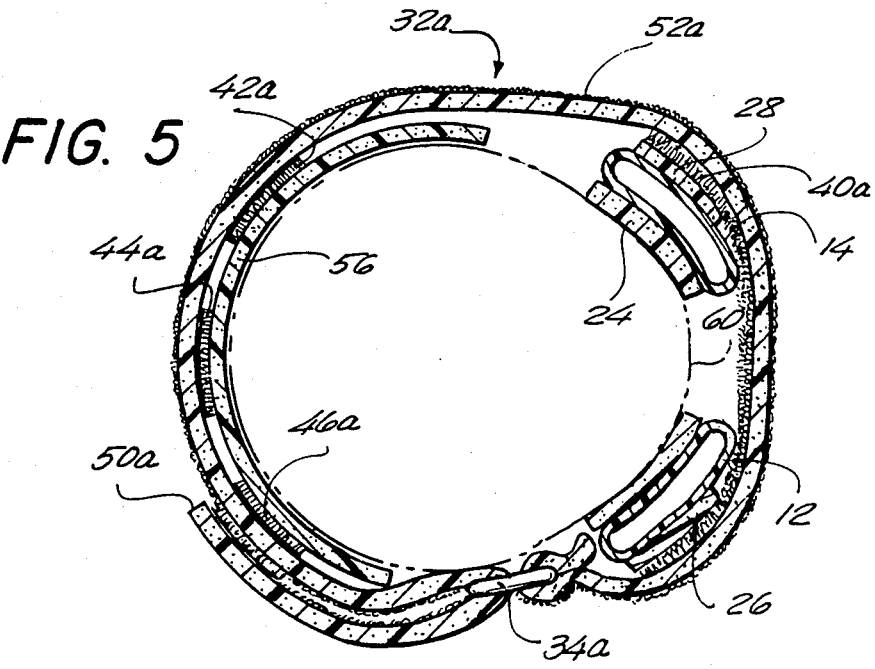
FIG. 5 is a sectional plan view taken along line 5—5 of FIG. 3.

Finally, a posterior pad 56 preferably of the type of material comprising open cell polyurethane foam laminated to front and rear layers of woven material capable of matingly engaging conventional hook-type fasteners, and commercially available under the trademark VEL-FOAM, is adapted to provide cushioning support to the rear of the knee as generally shown in FIGS. 2 and 3. Thus, the outer surfaces of pad 56 also comprise matable loop material so as to engage matable hook fasteners 42, 42a, 44, 44a, and 46, 46a on straps 32, 32a.

Before describing how the knee brace of the present invention is applied to the knee, it will be appreciated that upper strap 32 is fastened to air cell 10 by the mating action of VELCRO fastening element 40 and the pair of upper fastening elements 30 on stays 26, 28; whereas lower strap 32a is fastened to air cell 10 via the mating action of fastening element 40a with a pair of lower fastening elements 30 on stays 26, 28. To facilitate such fastening engagement, the longitudinal extent of fastening elements 40, 40a is sufficient to comfortably span the co-mating fastening elements 30 on stays 26, 28. Likewise, it will be appreciated that fastening elements 42, 44, 46 and 42a, 44a, 46a, are positioned on straps 32, 32a and spaced one from the other sufficiently to co-mate with posterior pad 56. These relationships are best seen in FIGS. 2-5.

With reference now to FIGS. 2-5, after straps 32, 32a are fastened to the air cell 10 (uninflated) and posterior pad 56 as described above, the knee brace may be fitted on the knee of leg 60 with the base portion 16 of the air cell engaging the knee above patella 62, and the opposed depending arm portions engaging corresponding opposed sides of the patella. When so positioned, the straps 32, 32a are adapted to encircle the leg 60 generally above and below the knee, respectively, as substantially shown to best advantage in FIG. 3. The free ends 50, 50a of upper and lower straps 32, 32a may then be inserted through rings 34, 34a, folded back and tensioned against the rings, and tightened until the straps are secured comfortably about the knee as schematically shown in FIG. 2. The free ends 50, 50a of straps 32, 32a may then be fastened in place by causing the hook fasteners 48, 48a to engage and co-mate with the loop material of outer ply 52, 52a.

The air cell may then be inflated by inserting tube 22 into the mouth of integral valve 18 and applying mouth pressure to the free open end of the tube. Supporting pressure will immediately be felt by the wearer against the regions of the knee surrounding the patella and co-extensive with air cell 10. If more support is desired, greater mouth pressure may be applied; however, this will increase the stiffness of the brace and may tend to limit somewhat the ability of the leg to undergo complete flexion. Simple trial and error inflation of air cell 10 will produce the desired combination of supporting pressure, flexion, and comfort. Withdrawal of tube 22 from the throat of valve member 18 will result in automatically sealing the air cell in its inflated condition.

Aside from the adjustment afforded the knee brace of the present invention by varying the initial inflation pressure of air cell 10, additional adjustment may be effected to further increase comfort or to compensate for variations in leg/knee size. Thus, in connection with one further mode of adjustment, the width of the opening between the depending arms 12, 14 of air cell 10, i.e. the patella opening, may be varied by disengaging the fastener 40a and lower strap 32a from its respective mating fastener at the bottom most ends of stiffeners 26, 28, moving the arm portions closer together or further apart as the case may be, and then re-engaging the matable fasteners to establish the new position of the arm portions relative to each other and, therefore, the size of the new patella opening.

In connection with still another further mode of adjustment, the posterior pad 56 may be disengaged from straps 32, 32a by disengaging matable fasteners 42, 42a, 44, 44a, and 46, 46a, repositioning the posterior pad circumferentially with respect to the straps and then re-engaging the matable fasteners when the posterior pad is in its new position.

As a result of the foregoing additional degrees of adjustment provided by the knee brace of the present invention, a standard dimensioned knee brace may be used to fit legs/knees of widely differing size. For example, in the preferred embodiment of FIGS. 1–5 it has been found possible to apply the knee brace to legs varying in diameter from about 14 inches to about 18 inches, i.e. the size common to most teenagers and adults.

In certain cases, it may be desirable to provide additional support to the knee joint particularly in the region proximal to and/or below the bottom portion of the patella, i.e. the infra patella region. The alternatively preferred embodiment shown in FIGS. 6 thru 13 includes, among other features and advantages, means for providing such enhanced patella support and will now be described in detail.

Figure 6:
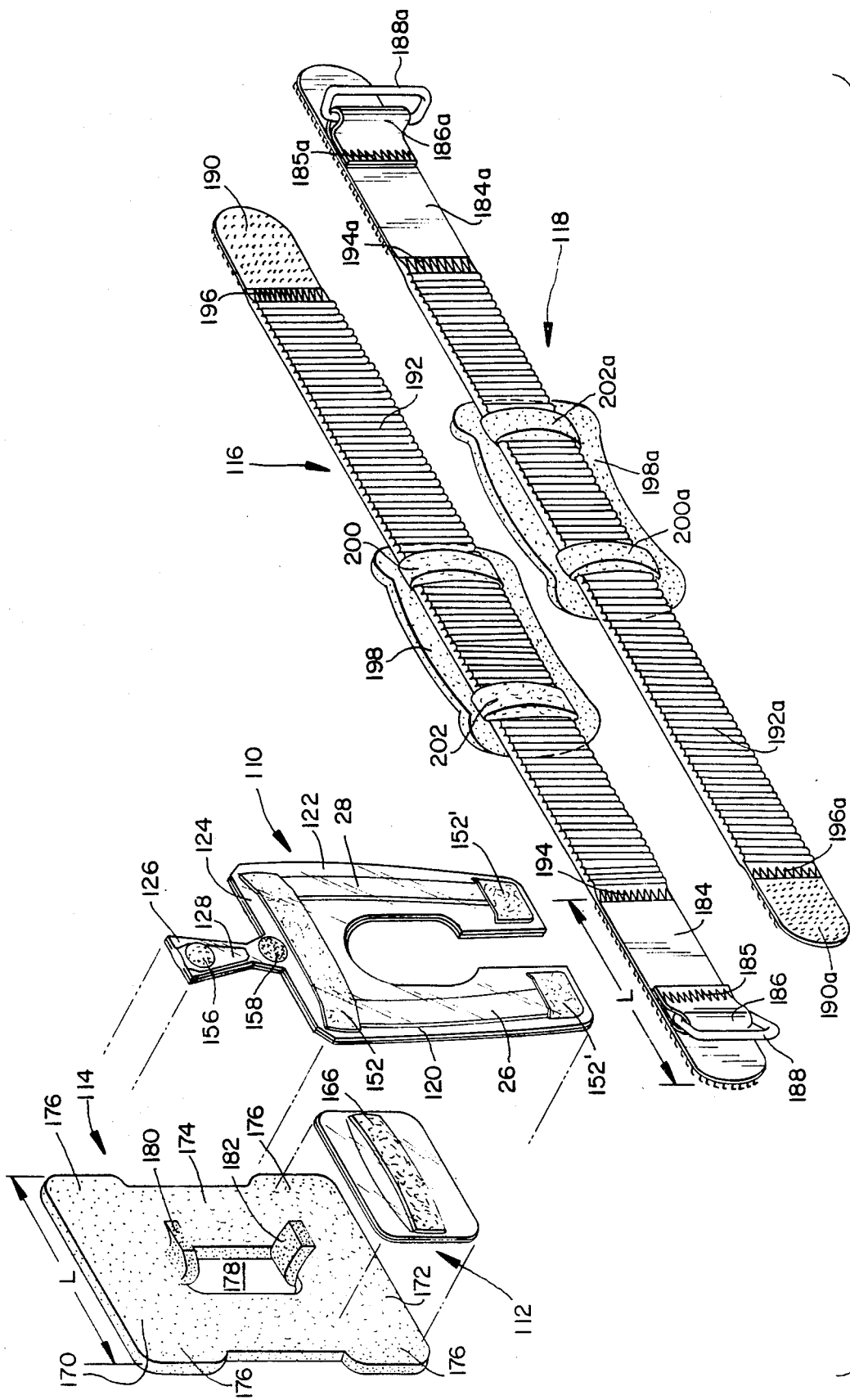
FIG. 6 is a schematic exploded perspective of the constituent parts of an alternatively preferred embodiment of the present invention.
Figure 7:
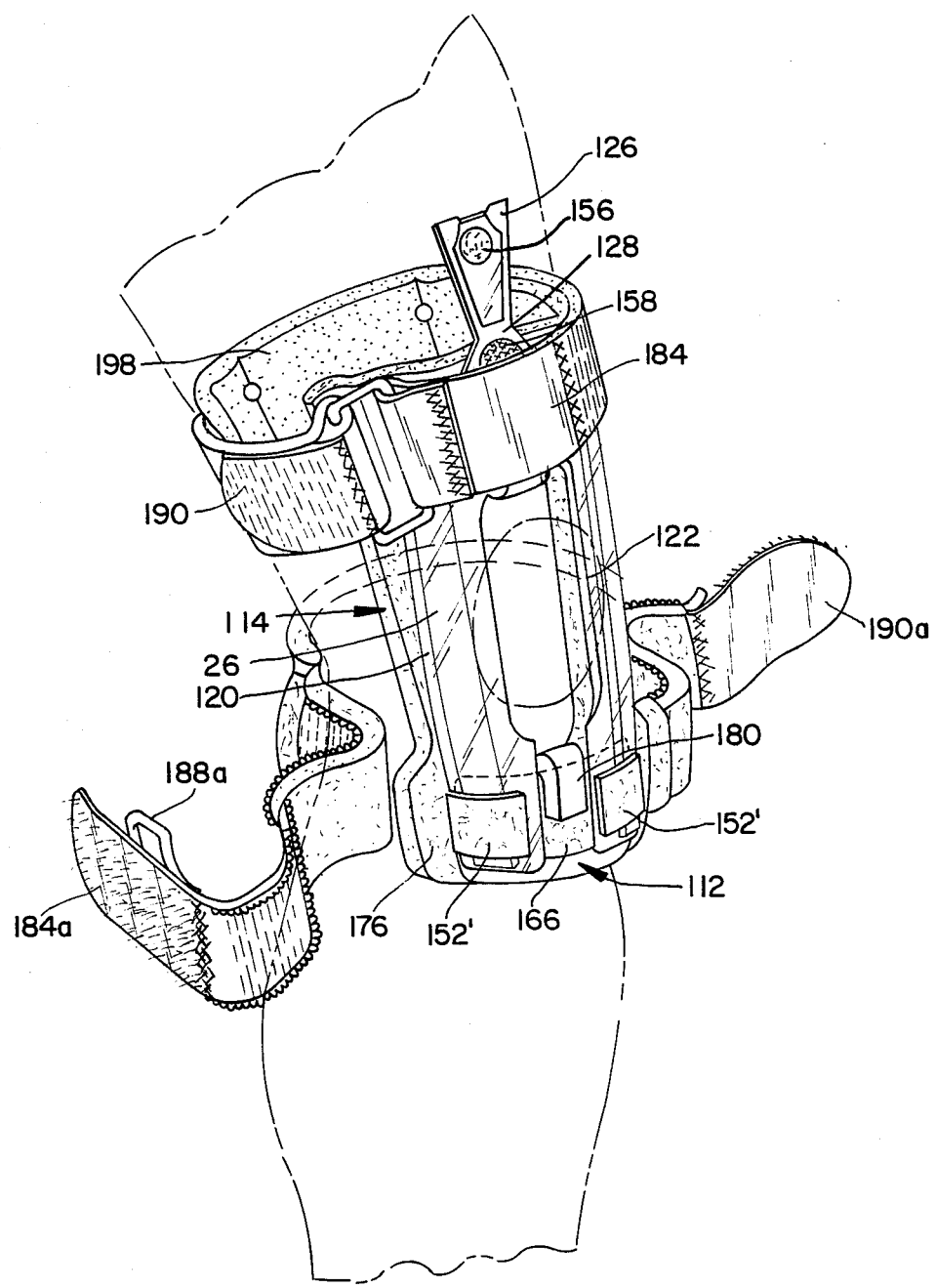
FIG. 7 is a perspective illustration of the alternatively preferred embodiment of invention fitted in place about an imaginary knee and having one fastening strap thereof folded away for the sake of clarity.

Referring initially to FIG. 6, the alternatively preferred embodiment of the knee brace according to the invention generally comprises a first inflatable air cell or bladder 110, a second or supplemental inflatable air cell or bladder 112, a backing member 114, and a pair of fastening straps or belts 116, 118. As will be described more fully below, these constituent parts include various fastening means to facilitate joinder and adjustment relative to one another whereby optimum comfort and efficacy may be achieved when the resulting knee brace is assembled and fitted about the knee of a subject (e.g. FIGS. 7–10).

As in the prior preferred embodiment, air cell 110 comprises a flexible, inflatable bladder having a pair of opposed arm portions 120, 122 depending from an upper base portion 124 to form generally an upside-down U-shaped configuration and is adapted to be fitted to the knee joint in such a manner that the base portion engages the knee proximally above the patella, the opposed arm portions straddle the patella, and the crown of the patella itself freely extends through the opening formed between the opposed arm portions and base portion.

An integral, self-sealing valve member 126 (preferably identical to valve 18) extends upwardly from base portion 124 via throat portion 128 for permitting selective pressurization or depressurization of the interior of air cell 110, preferably by means of mouth pressure transmitted through a flexible tube (e.g. tube 22, FIG. 1) the free end of which is capable of insertion through the valve opening and throat in the same manner as in the prior embodiment. Here again, withdrawal of the tube following entubation automatically seals the valve, maintaining the air cell at its intended internal pressure. In use, air cell 110 is capable of being selectively inflated in such manner to achieve an internal pressurization in the range of about 15 mm Hg to about 50 mm Hg. In most cases, an internal pressure in the range of 20 mm Hg to 35 mm Hg will be found to provide comfortable and effective patella support, and therefore, this range of pressurization of air cell 110 is mostly preferred.

Air cell 110 preferably is provided with the same pair of stays or stiffeners 26, 28 employed in the prior embodiment; however, in the alternatively preferred form of the invention, stays 26, 28 are supported relative to the respective arm portions 120, 122 by means of separate pockets integrally formed therewith. The pockets, in turn, are preferably formed by a separate or additional sheet of flexible material (e.g. polyvinyl chloride) bonded to the two sheets or plies forming air cell 110.

Figure 11:
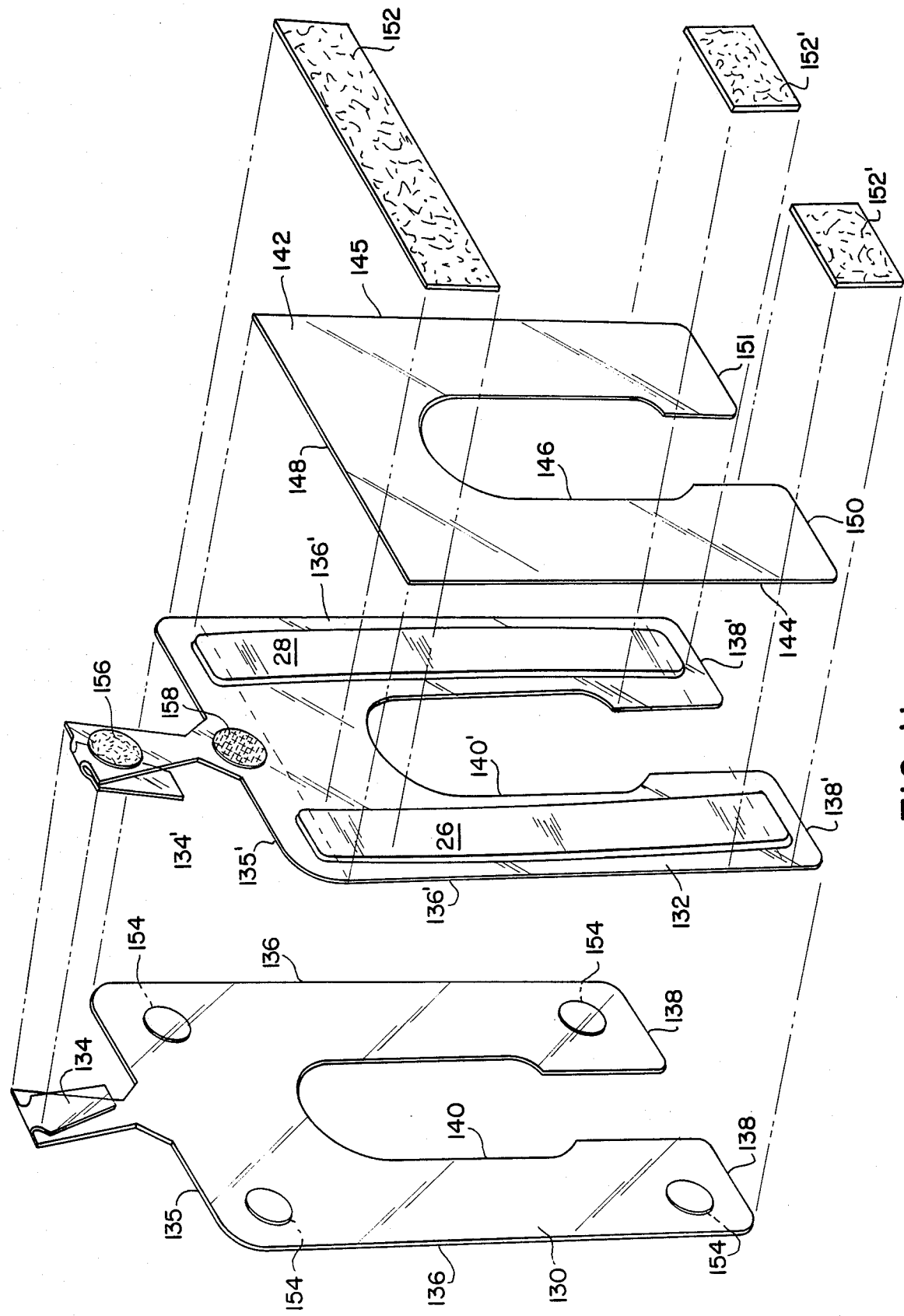
FIG. 11 is an exploded schematic view of the U-shaped air cell of the alternatively preferred embodiment of FIGS. 6 thru 10.

Thus, as shown to better advantage in FIG. 11, air cell 110 may be fabricated by superimposing a first sheet or ply 130 relative to a second ply 132, which has a shape conforming to the mirror image of sheet 130, such that valve flaps 134, 134′, top edens 135, 135′, side edges 136, 136′, bottom edges 138, 138′, and inner arcuate edges 140, 140′ are aligned relative to one another. A third sheet or ply 142 having a height or vertical dimension less than that of sheets 130, 132, as viewed in FIG. 11, next is aligned relative to the last-mentioned pair of sheets so that side edges 144, 145 are aligned with side edges 136, 136′, respectively, inner arcuate edge 146 registers with aligned inner arcuate edges 140, 140′; top edge 148 is spaced below top edges 135, 135′, and bottom edges 150, 151 are spaced above aligned bottom edges 138, 138′, respectively.

A heat sealing or bonding die having a configuration conforming to the commonly aligned marginal edges of the registered pair of sheets 130, 132 then is brought into engagement with the corresponding confronting edges or margins of all three sheets or plies comprising the stacked array to permanently bond or weld the edges together in a known manner (i.e. see U.S. Pat. No. 4,287,920, cited above). By this action, edge 144 of sheet 142 is commonly bonded along its entire extent to sheets 130, 132 in the region of aligned side edges 136, 136′; opposed edge 144′ of sheet 142 is commonly bonded along its entire extent to sheets 130, 132 in the region of the other opposed pair of aligned side edges 136, 136′; and inner arcuate edge 146 of sheet 142 is commonly bonded along its entire extent to sheets 130, 132 in the region of aligned inner arcuate edges 140, 140′. Top edge 148, and bottom edges 150, 151 of sheet 142 are not common to any aligned edge pairs of sheets 130, 132, and thus, are not engaged by the bonding die. Instead, top edge 148 and bottom edges 150, 151 remain free of sheet 132 to define openings through which stays 26, 28 may be inserted in a manner analogous to placing one's legs through the corresponding legs of a pair of trousers (i.e. edge 148 defines the "waist" whereas edges 150, 151 define the pair of leg openings).

Figure 12B:
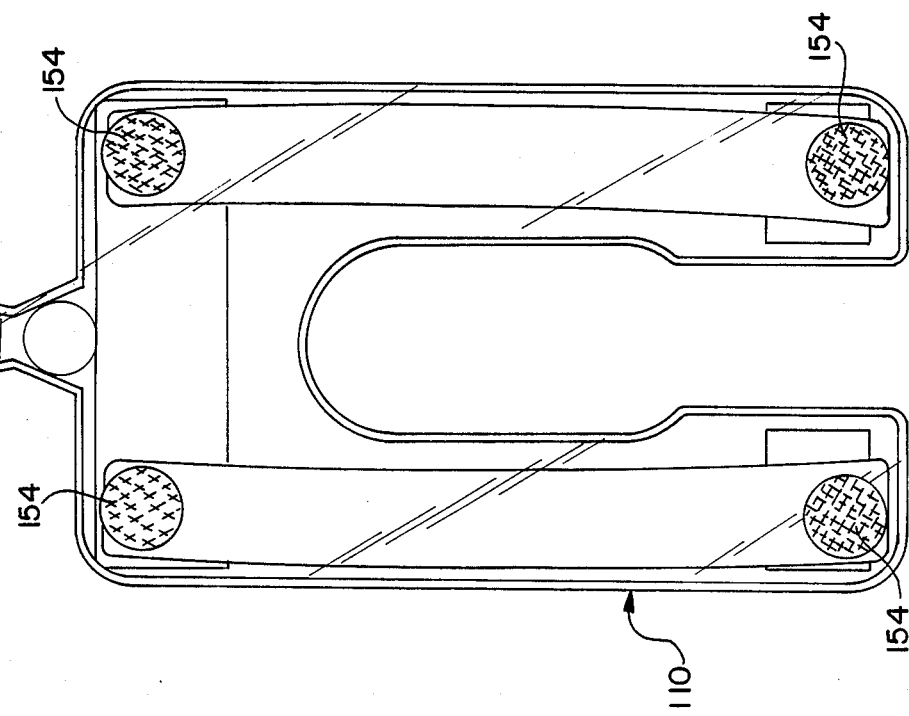
FIG. 12B is a rear elevation of the U-shaped air cell of FIG. 11.
Figure 12A:
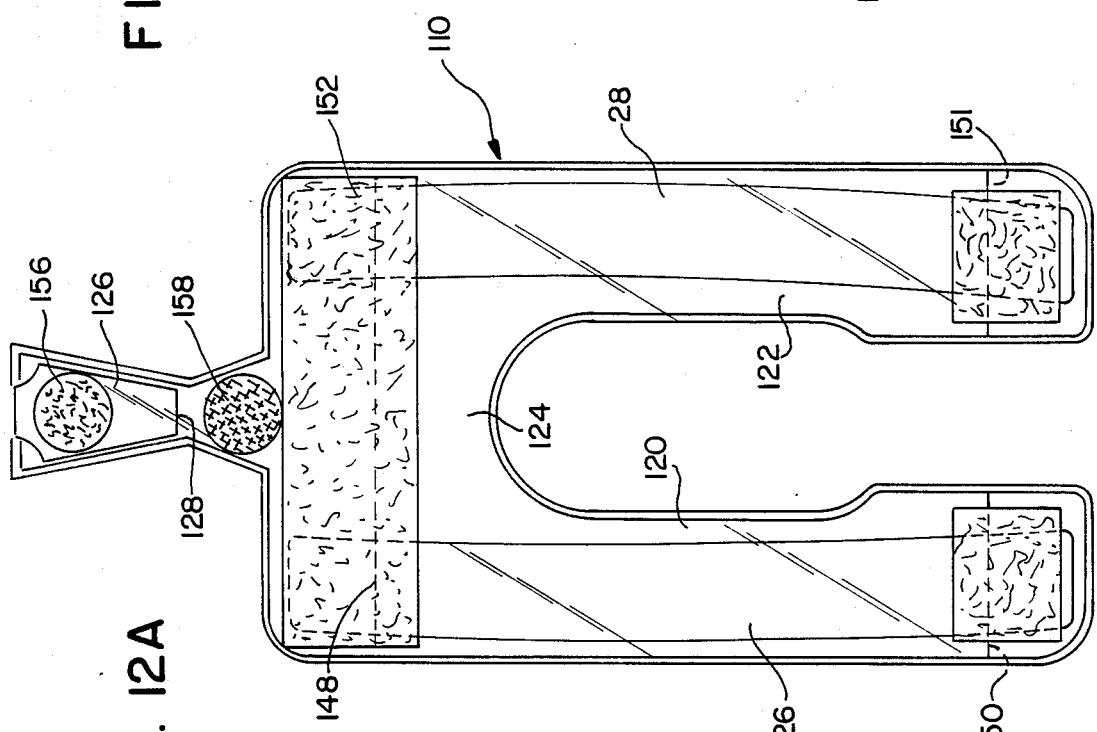
FIG. 12A is a front elevation of the assembled U-shaped air cell of FIG. 1.

After stays 26, 28 have been inserted in their respective pockets, assembly of air cell 110 is completed by attaching fastening strips 152, 152′ to the front side of the air cell and, fastening patches 154 to the reverse or rear side of the air cell as viewed in FIG. 11. Fastening strip 152 preferably comprises a flexible fabric having conventional matable loop-type fastening elements on its outwardly facing surface and is positioned to extend transversely of air cell 110 generally parallel to and below top edges 135, 135'. In addition, strip 152 is made wide enough to cover both the upper portions of stays 26, 28 and edge 148 substantially as shown in FIG. 12A. Strip 152 advantageously may be attached in place via a conventional pressure-sensitive adhesive coating applied to its rearwardly facing surface. In similar fashion, fastening strips 152', fabricated of the same material as strip 152, are adhesively affixed to extend parallel to and above bottom edges 138, 138' and to cover edges 150, 151 and the bottom most portions of stays 26, 28 respectively.

Fastening patches 154, on the other hand, preferably comprise four in number, are generally circular in shape and are of fabric material having conventional matable hook-type fastening elements on their outwardly facing surfaces. They too, are affixed in place substantially as shown in FIG. 12B, i.e. on the reverse side of air cell 110, utilizing a conventional pressure-sensitive adhesive compound.

Finally, a pair of somewhat smaller disk fabric fastener elements 156, 158, adapted to matingly engage one another, i.e. one is of the matable hook-type, the other of the matable loop variety, are adhesively secured to the upwardly extending selfsealing valve portion common to sheet 132 substantially as indicated.

In accordance with the alternative embodiment of the invention, the second or supplemental air cell 112 is substantially smaller in size than air cell 110; is generally rectangular in shape; has a longitudinal extent spanning both bottom portions of opposed arm portions 120, 122; and preferably, is pre-inflated to an internal pressure in the range of about 15 mm Hg to about 50 mm Hg, with an internal pressure in the range of about 20 mm Hg to about 35 mm Hg being mostly preferred.

Air cell 112 may be fabricated by superimposing a pair of similar rectangular sheets 160, 162 of flexible material (e.g. polyvinyl chloride) and bonding them together entirely along their common peripheral edge or margin 164 in the manner generally disclosed in my prior '920. In order to pre-inflate air cell 112 to its predetermined internal pressure, sheets 160, 162 preferably are bonded together along their common peripheral edges while simultaneously drawing a vacuum against the outwardly facing surfaces of one or both of the sheets. While pre-inflation of the smaller or supplemental air cell 112 offers the advantage of simplicity, it will be understood that alternatively, supplemental air cell 112 may be provided with the same self-sealing valve construction as air cell 110 wherein it may be inflated as desired to a pre-determined internal pressure utilizing tube 22 and mouth entubation, and/or the internal pressure thereof may be varied as and when desired. Conversely, air cell 110 (as well as air cell 10) likewise may be pre-inflated and such alternative modification is within the contemplation of the present invention.

Figure 13B:
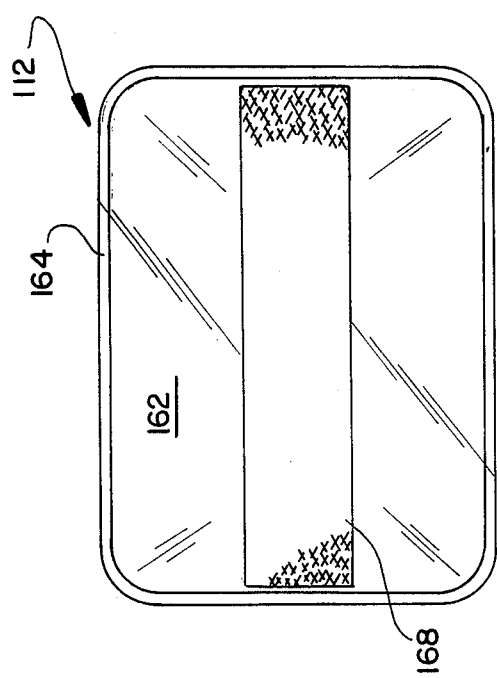
FIG. 13B is a rear elevation of the supplemental air cell of FIG. 13A.
Figure 13A:
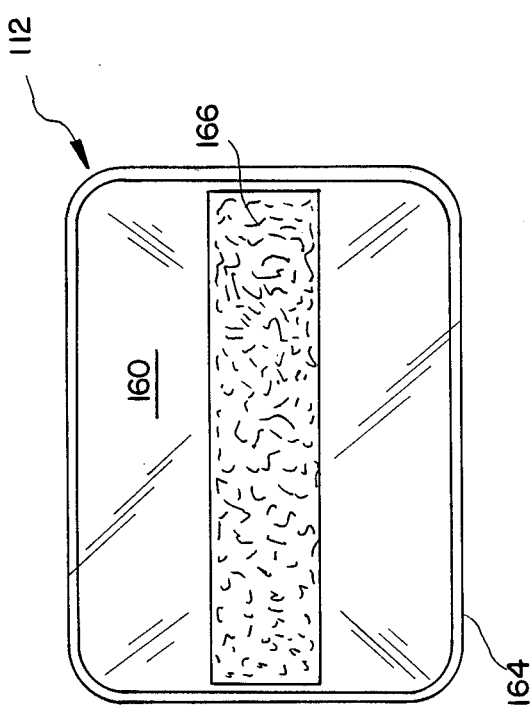
FIG. 13A is a front elevation of the supplemental air cell of the alternatively preferred embodiment of FIG. 6.

A pair of matable fabric fastener strips 166, 168 are disposed respectively on opposite sides of supplemental air cell 112, as more or less depicted in FIGS. 13A and 13B with each strip extending substantially entirely along the longitudinal extent of the air cell and having a height or vertical extent equal to or greater than the diameter of fastener disks 154 (air cell 110, FIG. 12A). Fastener strip 166 which faces outwardly from the side of air cell 112 defined by sheet 160 is of the matable hook-type whereas fastener strip 168 which faces outwardly from the side of air cell 112 defined by sheet 162 is of the matable loop variety with each of the strips being secured or affixed to the respective sides of the air cell by means of a conventional pressure sensitive adhesive or the like.

When air cells 110 and 112 are inflated as described above and the knee brace fitted in its intended position about the knee joint of a subject, air cells 110 and 112 are semi-compressible, i.e. each will conform to the irregular shape of the knee regions surrounding the patella, yet apply a uniform supporting force or pressure against the confronting regions of the knee engaged thereby.

Returning again to FIG. 6, backing member 114 provides support for air cells 110 and 112 and, as in the prior embodiment, further serves as a comfortable cushion between both air cells and the knee all of the while helping to avoid relative displacement therebetween especially during ambulation.

In its preferred form, backing member 114 is fabricated from a relatively thin sheet of flexible, resilient material such as open cell polyurethane foam, having front and rear layers of woven material laminated thereto which layers are capable of being matingly engaged by matable hook-type fastening elements. As mentioned above, a suitable material of this type is sold under the VELFOAM trademark and is widely available. As shown in FIG. 6, the backing member 114 comprises upper and lower sections 170, 172 which extend transversely beyond a central section 174 to form lateral extensions 176. A perforation in the shape of the letter "H" is centrally disposed in section 174, substantially as illustrated to define an opening 178 through which the crown of the patella may extend, and a pair of opposed, flexible tabs 180, 182 which may be bent or flexed upwardly and downwardly respectively, toward upper and lower sections 170, 172.

The relative shape and dimensions of backing member 114, air cell 110, and air cell 112 are such that when air cell 110 is juxtaposed relative to member 114, upper base portion 124 registers (i.e. is co-extensive) with upper section 170 (but for lateral extensions 176); arm portions 120, 122 are co-extensive with the lateral portions of section 174 on either side of opening 178, respectively; the bottom portions of arm portions 120, 122 co-extensively project onto equal areas of bottom section 172; and the opening defined by and between upper base portion 124 and downward depending arm portions 120, 122 substantially coincides with or registers with opening 178.

In addition, as will be further described below, when air cell 112 is located in its preferred position relative to member 114, air cell 112 reposes substantially co-extensively with bottom section 172 (but not lateral extensions 176).

In the alternatively preferred embodiment, backing member 114 is approximately 7 inches in length (top-to bottom) and about 5½ inches wide; air cell 110 has the same approximate dimensions as air cell 10 of the prior embodiment; and air cell 112 is approximately 3½ inches long and 2½ inches wide.

Fastening straps or belts 116, 118 are provided to maintain the air cell sub-assembly comprising first air cell 110, second or supplemental air cell 112 and backing member 114, securely in engagement with the knee joint and particularly, in engagement with the patella; and to facilitate a wide range of adjustment among the various parts of the sub-assembly and between these parts and the knee joint. As in the prior embodiment, straps 116, 118 are substantially identical and therefore a description of one will apply to the other with a letter "a" being used with like reference numerals to connote similarity of structure.

With reference to FIG. 6, strap 116 generally is of rectangular elongate shape and comprises at one free end thereof a first end portion 184 having a length or longitudinal extent indicated by the letter "L". Portion 184 is of a flexible fabric material having conventional matable hook-type fastening elements on its reverse or rearwardly facing side as viewed in FIG. 6. A fabric loop 186 carrying a fastening ring 188 is sewn to end portion 184 via a transverse seam 185 displaced longitudinally from the free end of portion 184 such that when the loop and ring are flattened against the outwardly facing surface of portion 184 in the direction of the free end, the ring does not extend beyond the distal extremity thereof.

At the opposed other free end of strap 116 is a second end or tongue portion 190 preferably of the same fabric material as first end portion 184, but having conventional matable hook fastening elements on its outwardly facing surface, substantially as indicated.

First and second free end portions 184, 190 are securely joined to the opposite ends of an intermediate portion 192 preferably by sewing along a pair of transverse seams 194, 196, respectively. Intermediate portion 192 advantageously consists of a strong, flexible, laminated (2 ply) fabric material, the outer layer of which comprises woven conventional matable loop-type fastener material, and the inner layer of which (rearwardly facing as viewed in FIG. 6) comprises polyurethane foam. Here again, it is noted that a suitable material of this construction is commercially available under the VELCRO trademark. In the alternatively preferred embodiment, the fastener straps or belts 116, 118 are about 24 inches in length, have a width of about 2 inches, and the "L" dimension of the first end portion 184 (or 184a) is approximately 5½ inches, which dimension, it will be observed, approximately is equal to the lateral extent of upper and lower portions 170 and 172 of backing member 114 (see FIG. 6).

Finally, a rectangularly shaped pad 198 of a suitable cushioning material (e.g. the same VELFOAM material as backing member 114 suffices nicely) is supported on intermediate portion 192 via a pair of spaced loops 200, 202, substantially as depicted. The precise axial position of pad 198 relative to intermediate portion 192 easily may be adjusted merely by sliding strap 116 relative to portion 192 and loops 200, 202, as desired. Pad 198 (and pad 198a) serve the same function as the posterior pad 56 of the preferred embodiment of FIGS. 1-5. In the alternatively preferred embodiment, pad 198 is approximately 6 inches long and 2½ inches wide.

Assembly of the alternatively preferred embodiment from its constituent parts may be effected quickly and easily. The supplemental air cell 112 first is fastened to section 172 of backing member 114 by engaging the matable hook elements on fastener strip 168 with the matable loop-type elements on the front surface of backing member 114. The air cell 112 should be positioned centrally of portion 172 so that i) lower lateral portions 176 extend substantially equally to the left and to the right beyond the distal transverse (vertical) edges of air cell 112; ii) the top longitudinal edge of air cell 112 generally is aligned with the bottom edge of the H-shaped perforation; and iii) the bottom longitudinal edge of air cell 112 nominally aligns with or extends slightly below the bottom edge of backing member 114, all as viewed in FIG. 6.

The primary air cell 110 may then be fastened to backing member 114 and air cell 112 by causing the two upper disk fasteners 154 (hook-type) to matingly engage the loop-type fastening elements on the outwardly facing surface of backing member 114, and by causing the two lower disk fasteners 154 to likewise matingly engage the loop fastening elements on the fastener strip 166 facing outwardly from the surface of air cell 112 defined by sheet 162.

When so assembled, base portion 124 attaches to portion 170 of backing member 114 and to air cell 112 so that (i) upper lateral portions 176 extend substantially equally beyond the lateral distal extremities of base portion 124; (ii) the top edge of base portion 124 aligns nominally with the top edge of backing member 114 and the integral valve and throat 126 and 128 extend above the top edge of backing member 114; (iii) the depending arm portions 120, 122 align nominally with the portions of section 174 to the left and to the right respectively of H-shaped perforation 178; and (iv) the distal bottom portions of arm portions 120, 122 overlap and engage correspondingly opposed lateral edge portions of supplemental air cell 112.

Figure 8:
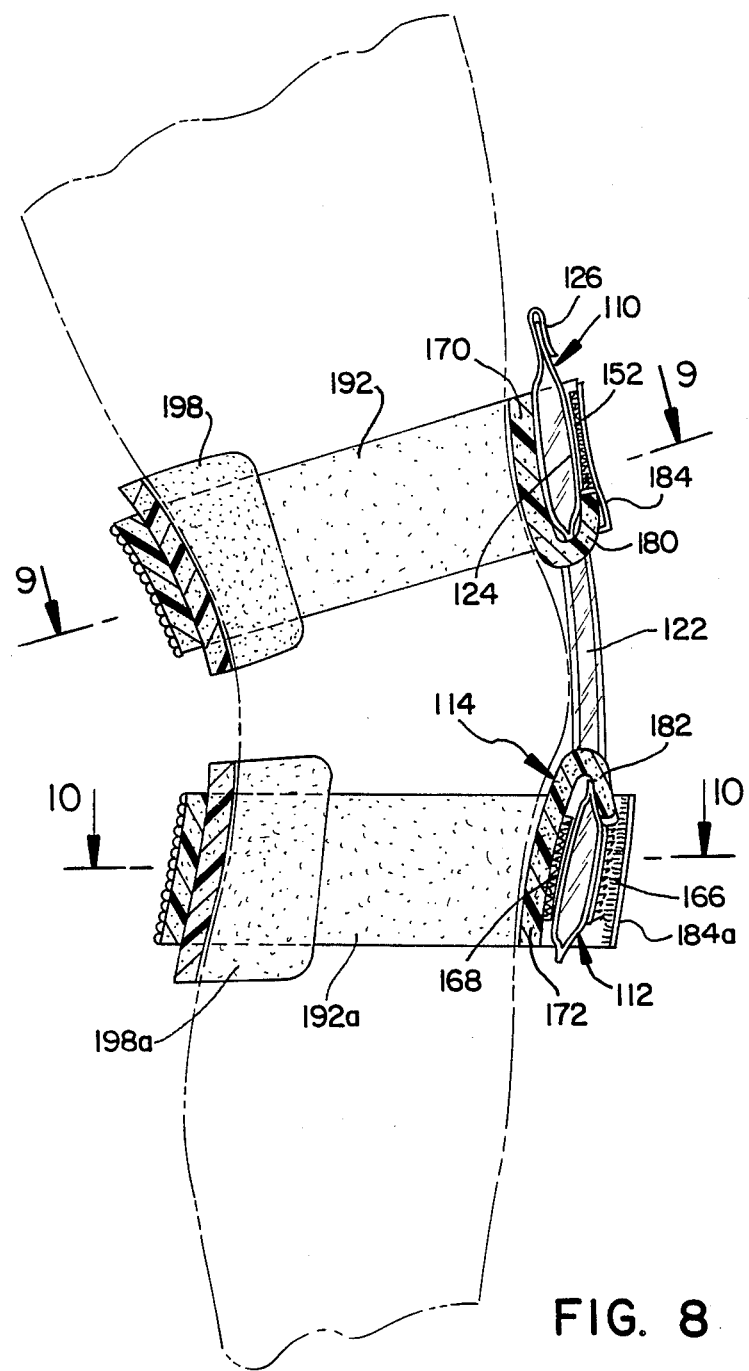
FIG. 8 is a view in elevation of a section defined by a vertical plane passing centrally through the knee brace embodiment and imaginary knee of FIG. 7.
Figure 9:
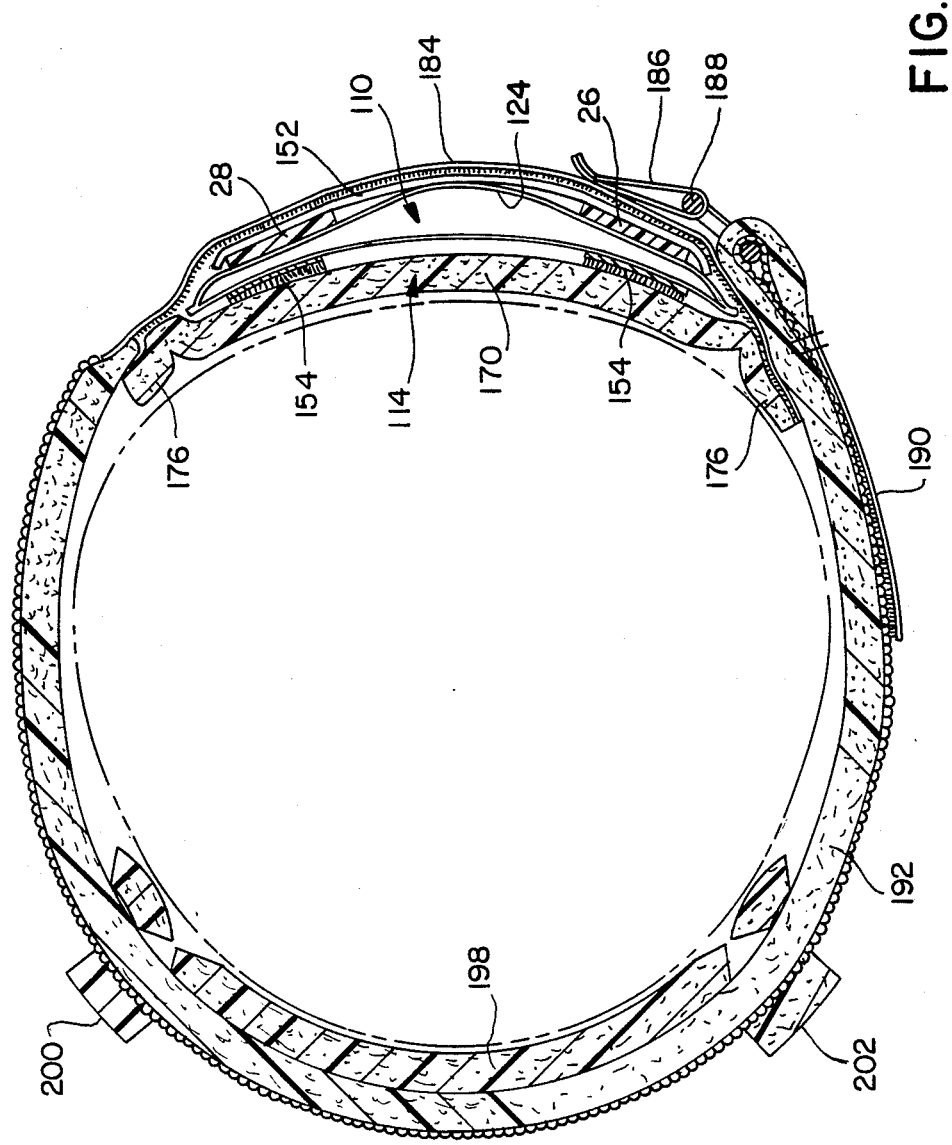
FIG. 9 is a sectional plan view taken along line 9—9 of FIG. 8.
Figure 10:
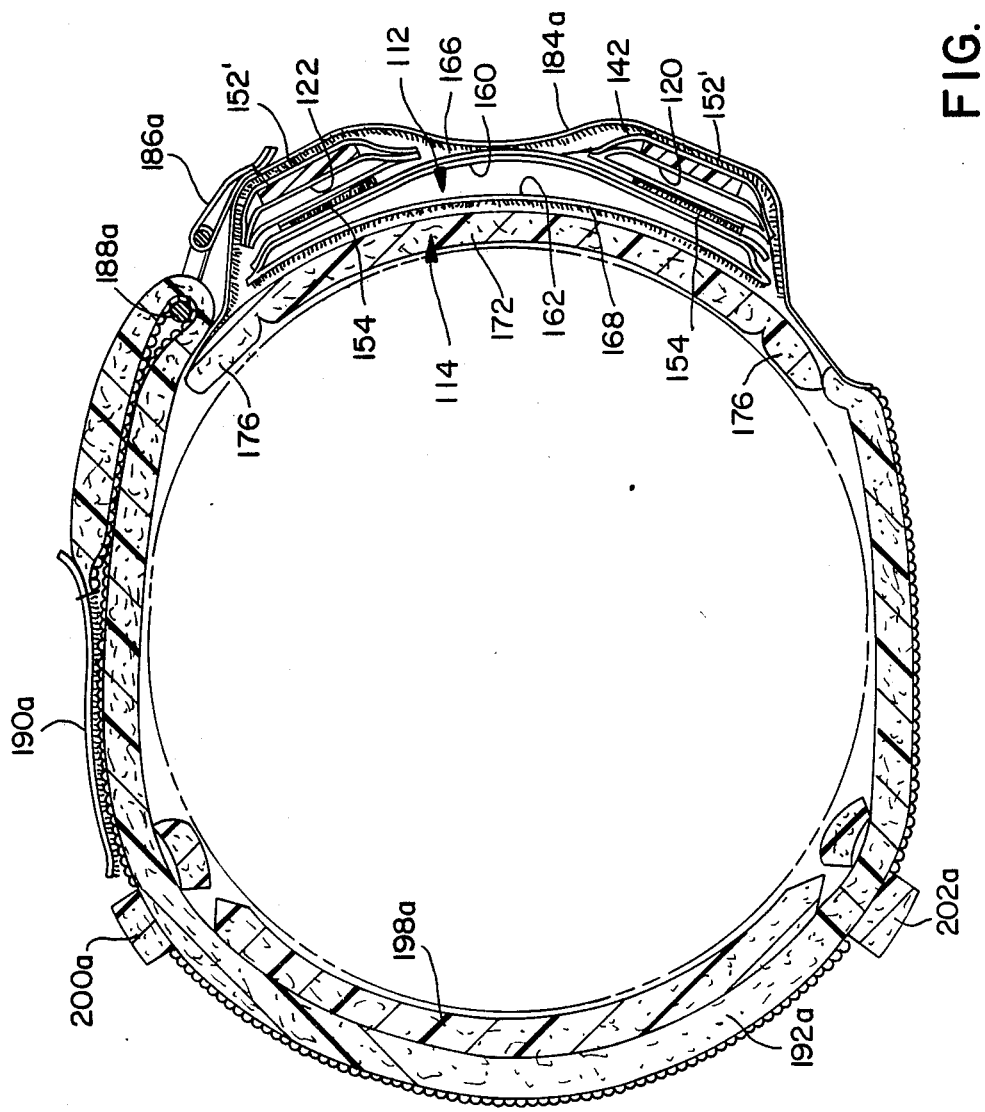
FIG. 10 is a sectional plan view taken along line 10—10 of FIG. 8.

Next upper fastener strap or belt 116 may securely be affixed to the air cell/backing member sub assembly by causing the hook elements on the rear surface of free end portion 184 to matingly engage the loop elements on fastener strip 152 as well as the loop elements on the confronting outwardly facing surfaces of lateral extensions 176 proximal to and extending beyond the sides of the upper base portion of air cell 110. See FIGS. 7 and 9. The upper tab 180, defining in part the Hshaped perforation 178 on backing member 114, also has conventional matable loop fabric on its rearwardly facing surface; hence, if it is bent upwardly before attaching portion 184 of strap 116, it will matingly engage the hook-type fastener elements on the rear surface of portion 184 and serve as additional securement for strap 116, air cell 110 and backing member 114, substantially as depicted in FIG. 8. When so attached, intermediate portion 192 and second free end portion 190 extends distally to the right as viewed in FIG. 6 whereupon these portions may be circumferentially wrapped about the leg above the knee joint and attached by inserting tongue 190 through loop 188, tensioning the strap 116 in a counterclockwise manner, and causing the hook fastener elements on the rear surface of tongue 190 to matingly engage the loop fastener elements on the outer surface of intermediate portion 192 as best viewed in FIG. 9.

Bottom fastener strap 118 similarly is affixed to the air cell/backing member sub-assembly, but extends in a direction opposite to that of upper fastener strap 116. Thus, first end portion 184a is attached by causing the hook fastener elements on the rear surface thereof to matingly engage (i) the matable loop fastening elements on both fastener strips 151'; (ii) the matable loop fastening elements on fastener strip 166 disposed between the bottom portions of arm portions 120, 122; and (iii) the loop fastening elements on the front surface of lateral extensions 176 proximal to and extending laterally beyond the sides of supplemental air cell 112 and the overlapping bottom portions of arm portions 120, 122 of air cell 110. Also, before attaching strap end portion 184a, tab 182 is flexed downwardly so that the loop fastener elements on its rear surface matingly engage the hook fastening elements on the rear surface of end portion 184a, between opposed arm portions 120, 122 thereby providing additional securement between the bottom strap, air cell 112 and backing member 114 (See FIGS. 7 and 8). When so attached, intermediate portion 192a and second free end portion 190a of strap 118 extend distally to the left as viewed in FIG. 6, whereupon these portions of the lower fastener strap may be circumferentially wrapped about the leg below the knee joint and attached by inserting tongue 190a through loop 188a, tensioning the strap 118 in clockwise manner, and causing the hook fastener elements on the rear surface of tongue 190a to matingly engage the loop fastener elements on the outer surface of intermediate portion 192a, as most clearly shown in FIG. 10.

It is well known that subluxation of the patella results in displacement outwardly or laterally of the knee joint. Hence, by having bottom strap 118 extend oppositely to upper strap 116 in the manner shown in FIGS. 6–10, this tendency is counteracted for a knee brace adapted to be worn on the right knee. In accordance with the present invention, straps 116, 118 are identical and interchangeable. Therefore, it is only necessary to reverse the relative directions of fastener straps 116, 118 if one desired to adapt the knee brace of the illustrated alternatively preferred embodiment for fitment about the left knee, i.e. the free end 190 of strap 116 will extend clockwise whereas the free end of 190a of strap 118 will extend counterclockwise as viewed in FIGS. 6–10. It is thus evident that the same knee brace construction, described above, may be utilized on either knee and separate "right" or "left" versions are obviated.

After straps 116, 118 are attached or fastened to the air cell/backing member sub-assembly as described above, the knee brace may be fitted on the knee of leg 60 as in the prior preferred embodiment. Thus, as diagramatically illustrated in FIGS. 7 and 8, the knee brace is positioned so that upper base portion 124 engages the knee through backing member 114 proximally above the patella, the opposed depending arm portions 120, 122 engage corresponding responding opposed sides of the patella through the backing member, the supplemental air cell engages the knee through the backing member in the infra patella region, and the crown of the patella extends comfortably through opening 178 and the co-extensive opening formed between the base portion, opposed arm portions, and supplemental air cell. Lower strap 118 then may be circumferentially tightened through loop 188a until supplemental air cell 112 comfortably provides desired compression support against the bottom portion of the patella, i.e. in the infra patella regions, and fastened in place as described above. Upper strap 116 may then similarly be circumferentially tightened in the opposite direction relative to strap 118 and fastened in place. Finally, air cell 110 may be inflated by inserting tube 22 into the mouth of integral valve 126 and by applying mouth pressure through the outer or free end of the tube. If air cell 112 has its own integral valve (rather than being pre-inflated), it too may be inflated in a similar manner at this juncture. As in the prior embodiment, sufficient mouth pressure is applied until the desired supporting pressure is felt by the wearer against the regions of the knee surrounding the patella and co-extensive with air cell 110 (or cell 112). Withdrawal of the tube from the throat 128 of valve 126 automatically seals the valve and maintains the knee brace in its inflated, supporting condition. Following withdrawal, valve 126 may be folded upon itself and neatly fastened in place by matingly engaging small disk fasteners 156, 158.

It has been found that the provision of the supplemental air cell 112, as described above, focuses effective supporting pressure in the infra patella region without requiring excessive circumferential tightening of fastening strap 118, i.e. the engagement pressure immediately underneath the air cell 112 is substantially greater than that at longitudinally spaced distances along strap 118 and displaced from air cell 112, for a given strap tension and inflation pressure of air cell 112. The alternatively preferred embodiment therefore, is quite effective, for example, in relieving the pain of chrondromalacia and Osgood-Schlatter's disease without causing undesirable constriction of portions of the knee in the vicinity of the patella.

It will be appreciated moreover, that owing to the manner of construction described above, the alternatively preferred embodiment is capable of the same wide range of adjustment achieved by the prior preferred embodiment. In addition, the position of supplemental air cell 112 may be adjusted relative to the depending arm portions 120, 122 and/or to the lower section 172 of backing member 114 by simply disengaging these parts and re-attaching in the newly adjusted position via matable fastening strips 166, 168 and 154. Further, as is evident from above, straps 116, 118 may be adjusted relative to the air cell/backing member sub-assembly via corresponding manipulation of the matable fastening elements on the rear surface of end portions 184, 184a, with mating fastening elements on backing member 114 and fastener strips 152, 152'; may be interchanged to convert the knee brace from one leg to the other; and, the position of pads 198, 198a may longitudinally be adjusted on each respective strap for optimum comfort. A particularly important advantage of the present invention resides in the flexibility afforded by providing fastener straps that are interchangeable one with the other and are selectively disengageably fastenable with respect to the air cell/backing member sub-assembly. Thus, although the alternatively preferred embodiment of FIGS. 6 thru 13 features fastener straps 116, 118 extending in opposite directions relative to one another; these fastener straps may be disengaged and re-attached so as to extend in the same direction with respect to each other as shown for example in the prior preferred embodiment illustrated in FIGS. 1 thru 5. In the arrangement where the straps extend in the same direction, the knee brace of the present invention is particularly effective in resisting subluxation of the patella with the direction of extent dictated by whether the knee brace is adapted to be fitted to the "left" or to the "right" knee, as will be apparent to those skilled in the art. The alternatively preferred embodiment therefore, also is capable of being manufactured in one standard size and form, yet is capable of being fitted to legs/knees of widely varying size, and being fitted to either the "right" or the "left" knee joint.

The preferred embodiments of the present invention have been described in detail merely for purposes of illustrating the principles of the invention and many obvious variations will occur to those of ordinary skill in the art. Therefore, the invention should be limited only by the spirit and scope of the claims appended hereto.

I claim:

1. A knee brace comprising first adjustable means for engaging the knee and providing support to the patella without hindering normal tracking movement thereof, second adjustable means for fastening said first means in engagement with the knee, third adjustable means for providing support to the infra patella region of the knee, wherein said first adjustable means comprises a flexible, semi-compressible support member, said flexible, semi-compressible support member comprising a base portion and a pair of depending arm portions thereby generally forming a U-shaped configuration, said support member being adapted for engagement with said knee such that the base portion engages the knee proximally above the patella and each of said arm portions engages the knee on opposed sides of the patella, respectively, and wherein said third adjustable means comprises a second flexible, semi-compressible support member at least a portion of which is adapted to be disposed between at least one of said arm portions and the infra patella region of the knee.

2. A knee brace adapted to promote normal tracking movement of the patella, comprising;

a first inflatable air cell, said first air cell having portions for applying cushioning support proximally above the patella; on opposed sides of the patella, and proximally below the patella, a second inflatable air cell, said second air cell being configured to apply cushioning support proximally below the patella, and a pair of circumferentially adjustable fastening straps, one of said pair of straps being adapted to maintain said first air cell in semi-compressed engagement with the knee proximally above the patella, and the other of said pair of straps adapted to maintain said second air cell and a corresponding portion of said first air cell in semi-compressed engagement with the knee proximally below said patella and wherein at least a portion of said second air cell is disposed between said knee and said corresponding portion of said first air cell.

3. The knee brace of claim 2 wherein said first air cell comprises valve means for selectively inflating same and said second air cell is pre-inflated to a pre-determined internal pressure.

4. The knee brace of claim 2 wherein said first and second air cells are attached to said pair of fastener straps and to each other via disengageable fastener elements, respectively.

5. The knee brace of claim 4 wherein said one of said pair of fastener straps extends longitudinally to encircle said knee above the patella and is disengagingly fastened co-extensively to a portion of said first air cell disposed proximally above said patella, and wherein said other of said pair of fastener straps extends longitudinally to encircle said knee below the patella, and is disengagingly fastened co-extensively to at least a portion of said second air cell disposed proximally below said patella.

6. A knee brace comprising first adjustable means for engaging the knee and providing support to the patella without hindering normal tracking movement thereof, second adjustable means for fastening said first means in engagement with the knee, third adjustable means for providing support to the infra patella region of the knee.

wherein said first adjustable means comprises an inflatable air cell, wherein said inflatable air cell comprises a base portion and a pair of depending arm portions thereby generally forming a U-shaped configuration, said air cell being adapted for engagement with said knee such that the base portion engages the knee proximally above the patella and each of said arm portions engages the knee on opposed sides of the patella, respectively, and wherein said third adjustable means comprises a second inflatable air cell at least a portion of which is adapted to be disposed between at least one of said arm portions and the infra patella region of the knee.

7. The knee brace of claim 6 wherein said air cell has associated therewith valve means for selectably admitting air to the interior of said air cell thereby inflating said air cell after said air cell has been fastened in engagement with the knee via adjustment of said second means.

8. The knee brace of claim 6 wherein said air cell further comprises a stiffening member attached to each arm portion respectively.

9. The knee brace of claim 6 wherein said depending arm portions have free ends respectively, said free ends being adapted to extend proximally below the patella, said second means comprises a pair of longitudinally extending flexible strap members adapted to be circumferentially fastened about the leg in the region of the knee, one of said strap members being adjustably fastened to said air cell base portion, and the other of said strap members being adjustably fastened to said air cell arm portions in the vicinity of their free ends.

10. The knee brace of claim 9 wherein said strap members and said air cell base portion and arm portions include mating fastening elements whereby each of said strap members may circumferentially be adjustably fastened to said air cell.

11. The knee brace of claim 10 wherein each of said strap members further includes adjustable fastening means enabling the circumferential tension in each said strap member to be adjusted after the strap member is fastened in place about the leg.

12. The knee brace of claim 11 wherein said further adjustable fastening means comprises a ring attached to one free end of the strap, and a VELCRO fastening element attached to the other free end of the strap.

13. The knee brace of claim 11 wherein a posterior pad is provided adapted to be fastened to said strap member.

14. The knee brace of claim 6 wherein said first mentioned air cell includes self-sealing valve means for admitting a pressurized medium into said air cell to inflate same to a pre-determined pressure, and wherein said second inflatable air cell is pre-inflated to a pre-determined internal pressure.

15. The knee brace of claim 14 wherein said second air cell further comprises adjustable fastening means for removably mounting said second air cell between said at least one arm portion and the infra patella region of the knee.

16. The knee brace of claim 15 further comprising cushioning means disposed between said first and second air cells on the one hand and said knee engaged thereby on the other hand, said first and second air cells having adjustable fastening means , respectively, for removably attaching said air cells to said cushioning means.

17. The knee brace of claim 16 wherein said second adjustable fastening means comprises means adapted to removably attach said second air cell between said cushioning means and said at least one arm portion of said first mentioned air cell.

18. The knee brace of claim 16 further comprising first and second strap fasteners adapted to circumferentially engage the leg of a subject above and below the knee joint respectively, said strap fasteners being adjustably attached to opposed portions of said first mentioned air cell, respectively, and to portions of said cushioning means proximal to said opposed portions of said first mentioned air cell, respectively.

* * * * *